(12) United States Patent
Hunt et al.

(10) Patent No.: US 9,361,657 B2
(45) Date of Patent: Jun. 7, 2016

(54) SYSTEM AND METHOD FOR QUICKLY OBTAINING MEDICAL INFORMATION

(71) Applicant: Endevr LLC, St. George, UT (US)

(72) Inventors: Brandon Hunt, St. George, UT (US); Josh Taylor, St. George, UT (US)

(73) Assignee: Endevr LLC, St. George, UT (US)

( * ) Notice: Subject to any disclaimer, the term of this patent is extended or adjusted under 35 U.S.C. 154(b) by 0 days.

(21) Appl. No.: 14/537,271

(22) Filed: Nov. 10, 2014

(65) Prior Publication Data

US 2015/0170307 A1   Jun. 18, 2015

Related U.S. Application Data

(63) Continuation of application No. 13/606,562, filed on Sep. 7, 2012, now Pat. No. 8,881,990.

(51) Int. Cl.
| | |
|---|---|
| G06K 19/06 | (2006.01) |
| G06Q 50/24 | (2012.01) |
| G09F 3/00 | (2006.01) |
| A44C 5/00 | (2006.01) |
| G06K 19/077 | (2006.01) |
| G06F 19/00 | (2011.01) |
| G06F 17/30 | (2006.01) |
| H04M 3/51 | (2006.01) |

(52) U.S. Cl.
CPC .............. *G06Q 50/24* (2013.01); *A44C 5/0015* (2013.01); *G06F 17/30879* (2013.01); *G06F 19/323* (2013.01); *G06K 19/06037* (2013.01); *G06K 19/07762* (2013.01); *G09F 3/005* (2013.01); *G06F 17/30861* (2013.01); *H04M 3/5116* (2013.01); *H04M 2242/04* (2013.01)

(58) Field of Classification Search
CPC .............................. G06K 7/1417; G06Q 50/24
USPC .......................................................... 235/494
See application file for complete search history.

(56) References Cited

U.S. PATENT DOCUMENTS

| | | |
|---|---|---|
| 3,864,856 A | 2/1975 | McManus |
| 4,857,716 A | 8/1989 | Gombrich et al. ............ 235/375 |
| 5,877,742 A | 3/1999 | Klink |
| 7,696,880 B2 | 4/2010 | Carmeli et al. ............ 340/572.1 |
| 8,135,597 B1 | 3/2012 | Tahan ................ 705/3 |
| 8,819,837 B2 * | 8/2014 | Lacey ............................ 726/26 |
| 2003/0016122 A1 | 1/2003 | Petrick |

(Continued)

FOREIGN PATENT DOCUMENTS

JP    2002-083062 A    3/2002

OTHER PUBLICATIONS

PCT search rpt and opinion PCT/US13/058150 (present case), Jan. 16, 2014.

*Primary Examiner* — Seung Lee
(74) *Attorney, Agent, or Firm* — Phillips Ryther & Winchester; Matthew D. Thayne

(57) ABSTRACT

A medical bracelet, wrist-band device, watch, piece of jewelry, or any other worn item contains a OR code for fast scanning by emergency first responders, ER teams or any other medical personnel. Scanning the QR code with a handheld device like a smartphone results in immediate retrieval of pertinent medical information either directly from the QR code, or from a dedicated website. Further security of medical information can be provided by a numerical or alphanumerical patient ID. and a PIN that can be printed on the device for fast access.

19 Claims, 5 Drawing Sheets

(56) References Cited

U.S. PATENT DOCUMENTS

| | | | |
|---|---|---|---|
| 2007/0203751 A1* | 8/2007 | Koblasz | G06F 19/323 705/2 |
| 2011/0093296 A1 | 4/2011 | Klink | |
| 2012/0049505 A1 | 3/2012 | Yokoyama | |
| 2013/0126601 A1 | 5/2013 | Lee | 235/375 |
| 2013/0268292 A1 | 10/2013 | Kim et al. | 705/2 |
| 2013/0290013 A1 | 10/2013 | Forrester | 705/2 |

\* cited by examiner

PRIOR ART

George W. Jones

Address

Phone

Email

Emergency Contacts

Vitals

Gender

DOB

Height/Weight

Blood Type

Donor

Medical Profile

MAJOR MEDICAL CONDITION

Allergies

Meds

Insurance

Physicians

SYSTEM AND METHOD FOR QUICKLY OBTAINING MEDICAL INFORMATION

This is a continuation of application Ser. No. 13/606,562 filed Sep. 7, 2012, now U.S. Pat. No. 8,881,990 issued Nov. 11, 2014. application Ser. No. 13/606,562 is hereby incorporated by reference in its entirety.

BACKGROUND

1. Field of the Invention

The present invention relates generally to emergency medical identification devices and more particularly to a system and method for quickly obtaining a person's medical information using a QR code on a wristband or other worn object.

2. Description of the Prior Art

It is well-known in the art for people to wear wrist bands containing medical information. For example, diabetics have worn bands or carried tags to notify of their illness since there is a certain probability that the diabetic might be found unconscious. For years, patient identification has been placed on a bracelet or wrist-band known as a MEDICALERT bracelet or pendent. This is well known to ER and first-responder personnel, and it is one of the first things they look for. However, a MEDICALERT device usually only provides a telephone number that can be called for the patient's medical information.

U.S. published application 2011/0093296 describes a device that resembles a wristwatch that can store and instantly display complete medical information about a patient.

U.S. Pat. No. 3,864,856 teaches medical information being on a card held in a compartment of a watch or wrist-strap.

U.S. Pat. No. 5,877,742 teaches a medical identification bracelet that has electronic circuitry to display detailed patient medical information.

U.S. published application no. 2003/0016122 teaches an RFID tag worn by a person that transmit coded information allowing access to medical information.

The United States Dept. of Health and Human Services is calling for national coordination for health information technology. The government is proposing electronic wrist-bands that can contain information on over 125 chronic medical conditions.

The problem with electronic wrist-bands or other electronic devices is that they require periodic battery replacement or charging, are subject to damage from blows or shocks, and will usually not function after being placed in water. It would be advantageous to have a wrist-band that did NOT contain any electronics, but could harness the power of the modern electronic/telecommunications world, especially the cellular telephone or smartphone, to immediately retrieve critical medical information by first responders and ER teams.

A QR code (Quick Response Code) is well-known and heavily used today. A QR code is a small square coded patch (see FIG. 2) resembling a 2-dimensional bar code (but different) that is designed to be viewed by the camera or image sensor in a cellular smartphone, pad or other portable device. Typically, the QR code simply returns a URL that the user's browser then moves to. Alternatively, QR codes can be used to initiate the downloading of applications (Apps.).

[Unlike the older bar codes that were designed to be mechanically scanned by a narrow beam of light, the QR code is detected as a 2-dimensional digital image by a semiconductor image sensor and is then digitally analyzed by a programmed processor. The processor locates three distinctive squares at the corners of the image, normalizes image size, orientation, and angle of viewing with the aid of a smaller square near the fourth corner. The small dots are then converted to binary numbers and validity checked with an error-correcting code.] (From Wikipedia.com).

Since most first responders and ER personnel carry cellular telephones, and especially smartphones, and because almost every future cellular telephone will be able to read a QR code, it would be very advantageous to combine the quick access and response of a QR code with a medical bracelet or wrist-band, or any other worn item that can hold a QR code.

SUMMARY OF THE INVENTION

The present invention relates to a new type of medical bracelet, wrist-band device, watch, piece of jewelry (or any other worn item) that displays a QR code for fast scanning by first responders, ER teams or any other medical personnel. Scanning the QR code with a telephone or other handheld device results in immediate retrieval of pertinent medical information from a dedicated website or directly from the QR code itself. Further security of information can be provided by a numerical or alphanumerical patient ID, and a PIN that can be printed on the device for fast access.

The device can be a simple bracelet, or it can be a stylish piece of jewelry by having a designer shape. It can also being a man's or woman's wristwatch, a pendent, a piece of jewelry, or any other worn item including an ion or negative ion bracelet, or magnet bracelet known in the art.

The inside or outside of the device can have a highly visible, and easily scannable, QR code. It can also have instructions to scan for medical information, a patient ID., a PIN number and/or a telephone number that can be called as a backup. Other optional information can be included.

DESCRIPTION OF THE FIGURES

Attention is now directed at several drawings that illustrate features of the present invention.

Several drawings and illustrations have been presented to aid in understanding the present invention. The scope of the present invention is not limited to what is shown in the figures.

DESCRIPTION OF THE PREFERRED EMBODIMENT

The present invention relates to a medical wrist-band, bracelet, watch, piece of jewelry, pendent, necklace or any other worn device holding a QR code for fast scanning to obtain emergency medical information about the wearer.

Figure 1:
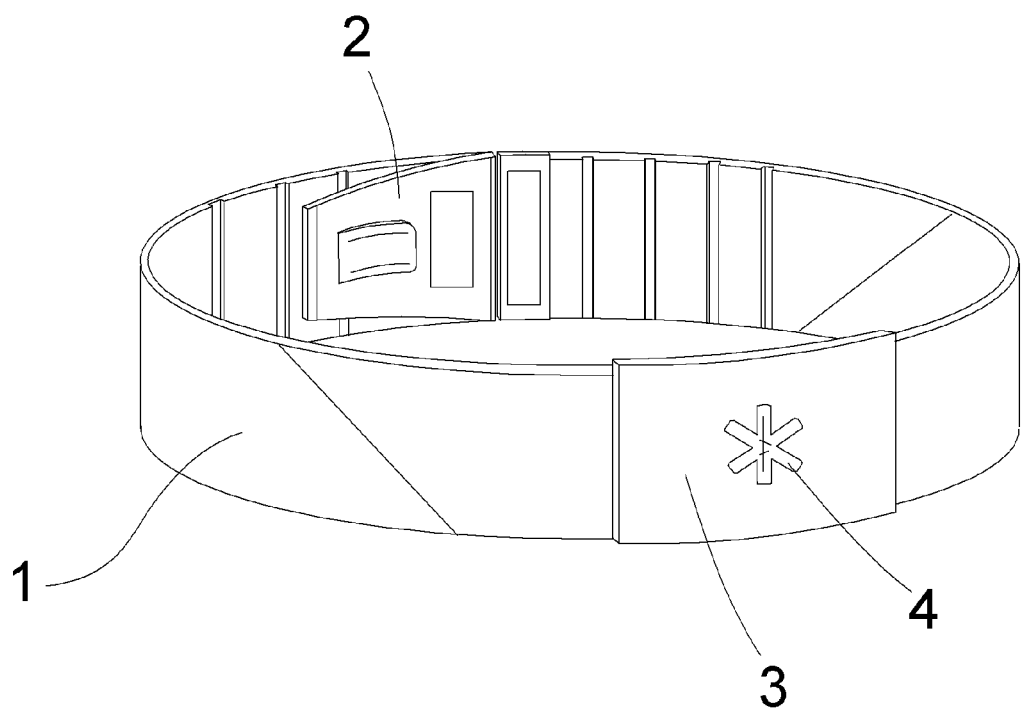
FIG. 1 shows a profile view of a wrist-band embodiment of the present invention.

FIG. 1 shows a wrist-band embodiment of the invention. A band 1 buckles around the wrist 2 and carries a tag 3 optionally displaying a medical symbol 4. The inside of the tag 3 displays a QR code along with supplementary information.

Figure 2:
FIG. 2 shows a prior art QR code.

FIG. 2 shows a prior art QR code. The code has three alignment symbols which can be seen in FIG. 2 as larger squares on the upper and lower left side and the right top. QR codes follow one of a family of standards, and are readable by millions of smart telephones today. In the future, almost every handheld telephone, pad device or computer will be able to scan and read them.

According to Wikipedia, [QR codes, formerly confined to industrial uses, have in recent years become common in consumer advertising and packaging. Users with a camera phone equipped with the correct reader application can scan the image of the QR Code to display text, contact information, connect to a wireless network or open a web page in the telephone's browser. QR Codes may also be linked to a location to track where a code has been scanned. The application that scans the QR Code can also optionally retrieve geographic information by using the GPS receiver in the telephone].

Figure 3:
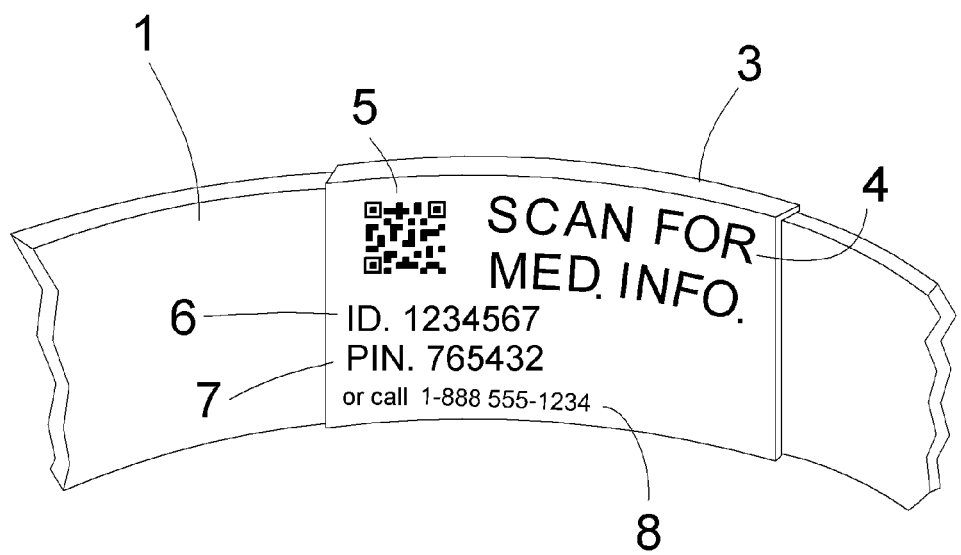
FIG. 3 shows the inside of the wrist-band tag from FIG. 1 with the QR code visible.

FIG. 3 shows the inside of the tag 3 in the wrist-band embodiment of FIG. 1. The tag 3 can display a QR code 5, instructions to scan 4 (so that a responder knows he or she will receive medical information), an optional patient ID 6, an optional PIN 7 and an optional backup telephone number 8.

Upon scanning the QR code 5, the responder may be supplied with one or both of two different types of information. The first type is information encoded in the QR code itself. Newer versions of QR codes can contain much more information than older versions. The second type of information is the URL of a webpage. The responder's online browser can immediately go to that webpage.

The first type of information might be a simple message identifying a major condition such as "DIABETIC" or it might be more detailed. The second type of information can be detailed medical information from a database provided on the webpage. The present invention allows one or both types of information to be supplied to the responder. In the case of a webpage, the responder can query the webpage for further information if necessary.

When a webpage is used, extremely important information about that patient could be supplied instantly by the website upon entry. This can be accomplished by encoding the patient ID. and optionally the PIN in the QR code itself. Alternatively, the responder could be asked to enter the patient ID and PIN, or, in some embodiments, only the patient ID. The tradeoff is security of patient information against speed in which the responder can obtain necessary information. Encryption of information in the QR code or of information transmitted or stored on the website can be used to enhance security.

Figure 4:
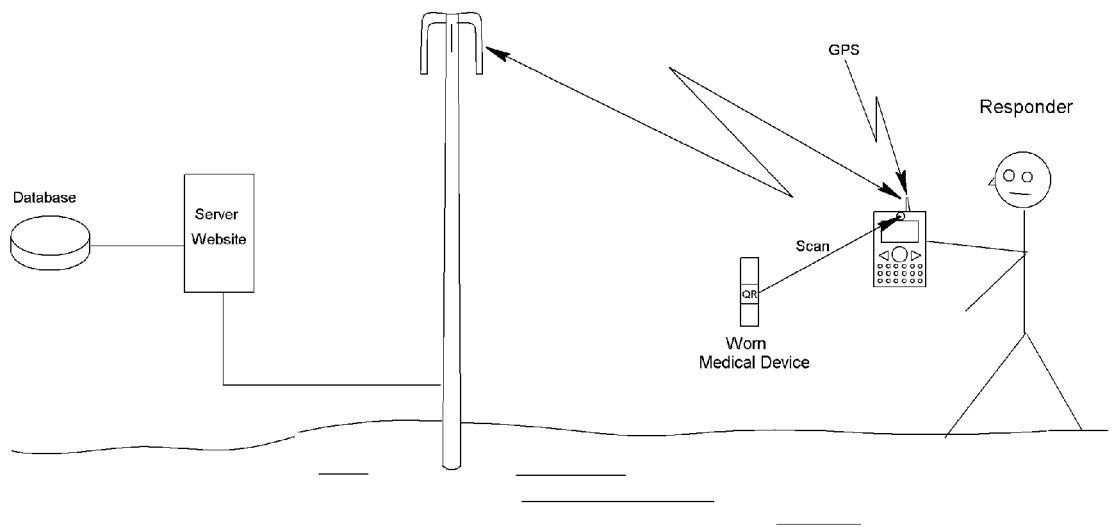
FIG. 4 shows the transmission of location information after scanning.

The webpage service can also optionally provide hospital pre-notification that the QR code has been scanned by a particular responder. Alternatively, the responder can initiate hospital pre-notification on the webpage. In some embodiments of the invention, the telephone can determine the geographic location of the responder at the time the QR code is scanned (using the telephone's GPS or other location services). This location data could be forwarded along with hospital pre-notification. A database provided either by the website or the App. in the telephone could choose (or be preprogrammed with) the correct hospital where the patient will be taken based on geographic location. This is shown in FIG. 4. A responder scans the QR code, which returns a URL. Geographic information is sent to the website, and medical information is sent from the website to the responder.

The backup telephone number on the worn device could be answered by a 24 hours emergency call center. In this case, a live person can provide data to the responder and optionally hospital pre-notification.

Figure 5:
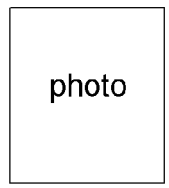
FIG. 5 shows the display that can be returned to a responder after scanning.

The webpage can be supplied in a form that is easily readable on a cellular telephone. An example of this is shown in FIG. 5. Here, the returned profile has the person's name, photo, address, phone, email, emergency contacts, vitals, medical profile including MAJOR MEDICAL CONDITIONS, allergies and medications, insurance information and names and address of physicians. Many variations are possible; however, FIG. 5 illustrates the basic layout of a returned webpage. Any format or content of a returned webpage is within the scope of the present invention.

The user, when not in an emergency situation, can easily logon to the website to update their patient information. Doctors and other healthcare professionals can also optionally logon to the website to update patient data. Alternatively, patient data could be transferred to the website (with permission of the patient) from a physician's or hospital's database. This type of information entry or transfer is particularly important to make sure the medications currently being taken by the patient are correctly entered since many drugs have similar, but slightly different names.

In different embodiments of the present invention, the QR code can be displayed on the outside of the device for quicker access, or on both the inside and outside.

While most smartphones have applications (Apps.) that can already scan a QR code and access a URL, the present invention can also supply custom applications to responders to carry in there telephones. The specialized Apps. could display local information contained in the QR code and perform other services such as sending location information as has been discussed.

Some embodiments of the invention can have more than one QR code so that more data can be put into the QR code for use by responders. Maximum local information is particularly important for emergencies such as hurricanes, tornadoes, floods and other natural disasters that affect large numbers of people and may take both electricity and cellular service down. In these cases, the telephone browser may not work, and websites may not be accessible. However, as long as the telephone has battery power, it can scan the QR code and display the information stored in the code. This locally stored and displayed information can be the essential medical information needed by the responder.

The present invention is a system and method that can vastly speed up the flow of emergency medical information into the hands of first responders and ER teams by using a quickly and easily scanned QR code on a worn device like a bracelet, watch or piece of jewelry.

Several descriptions and illustrations have been provided to aid in understanding the present invention. One with skill in the art will realize that numerous changes and variations may be made without departing from the spirit of the invention. Each of these changes and variations is within the scope of the present invention.

The invention claimed is:

1. A system for providing medical information, comprising:
   a medical bracelet, watch or piece of worn jewelry comprising a QR code on at least one surface of the medical bracelet, watch or piece of worn jewelry that is configured to be scanned by a handheld device, the QR code containing a URL that includes information related to a wearer, wherein the medical bracelet, watch or piece of worn jewelry further comprises at least one of a backup telephone number for obtaining medical information related to the wearer and a security code, wherein the handheld device is configured to execute instructions to perform a location determination, and wherein, upon being scanned by the handheld device, the QR code is configured to execute computer instructions in the handheld device to access the URL; and a remote server configured to display medical information relating to said wearer by addressing a website represented by the URL, the remote server then transmitting the medical information back to the handheld device, wherein the computer instructions cause the handheld device to display the medical information.

2. The system of claim 1 wherein said remote server is configured to issue a hospital pre-notification.

3. The system of claim 1, wherein said location determination is transmitted to the remote server.

4. The system of claim 1, wherein the handheld device is further configured to execute instructions to determine a closest hospital based on said location determination.

5. The system of claim 4 wherein at least one of the handheld device and the remote server is configured to issue a hospital pre-notification to the closest hospital.

6. The system of claim 1, wherein the security code comprises a PIN number.

7. A worn item for obtaining medical information, comprising:
   an affixed QR code positioned on the worn item containing a URL that includes information pertaining to a wearer of the worn item;
   at least one of a backup telephone number for obtaining medical information related to the wearer and a security code for obtaining medical information related to the wearer, wherein, upon being scanned by a handheld device, the QR code is configured to execute executable instructions in the handheld device to access the URL, wherein said executable instructions are further configured to access the URL contained in the QR code on a remote website and to receive and display medical information from the remote website pertaining to the wearer, wherein the handheld device comprises an application computer program, and wherein said application computer program is configured to determine a location of said handheld device and send it to a server associated with the remote website.

8. The worn item of claim 7 wherein at least one of the handheld device and a server associated with the website is configured to send a hospital pre-notification to a predetermined hospital.

9. The worn item of claim 7, wherein the server is configured upon receiving information from said QR code and receiving said location determination from the handheld device to send a hospital pre-notification to a closest hospital.

10. The worn item of claim 7 wherein said medical information is encrypted on the remote website.

11. The worn item of claim 7 wherein the medical information includes a photograph of the wearer.

12. The worn item of claim 7 wherein the medical information comprises a name, photograph, address, emergency contacts, vitals, and a medical profile including medical conditions, allergies and medications.

13. The worn item of claim 7, wherein the worn item comprises a medical bracelet.

14. A method for communicating medical information to first responders, the method comprising the steps of providing a medical item having an affixed QR code, wherein the medical item further comprises at least one of a backup telephone number for obtaining medical information related to a wearer of the medical item and a security code for obtaining medical information related to a wearer of the medical item;
   executing an application (App) on a handheld device to first responders by scanning said QR code, wherein said App further provides a hospital pre-notification to a particular hospital based on said medical information received from a remote server; and
   receiving and displaying medical information related to the wearer on the handheld device.

15. The method of claim 11, further comprising performing a location determination.

16. The method of claim 15, further comprising transmitting the location to a remote server.

17. The method of claim 16, further comprising transmitting information related to a closest hospital.

18. The method of claim 14, wherein the medical item comprises at least one of a medical bracelet, a wrist-band device, a watch, and a piece of worn jewelry.

19. The method of claim 14, further comprising transmitting an ID associated with the wearer to a remote server.

* * * * *